United States Patent [19]

Richter et al.

[11] Patent Number: 4,648,004
[45] Date of Patent: Mar. 3, 1987

[54] METHODS FOR DETECTING A MAGNETIC PREORIENTATION IN MECHANICAL PARTS AND FOR MAGNETIZING THE PARTS UTILIZING SUCH DETECTION METHOD, AND AN ASSOCIATED DEVICE FOR MAGNETIZING THE PARTS IN ACCORDANCE WITH THESE METHODS

[75] Inventors: Martin Richter, Marloffstein; Reinhold Piesch, Nuremberg, both of Fed. Rep. of Germany

[73] Assignee: Siemens Aktiengesellschaft, Berlin and Munich, Fed. Rep. of Germany

[21] Appl. No.: 786,390

[22] Filed: Oct. 10, 1985

[30] Foreign Application Priority Data

Oct. 26, 1984 [DE] Fed. Rep. of Germany ....... 3439341

[51] Int. Cl.$^4$ ............................................. H01H 47/00
[52] U.S. Cl. ....................................................... 361/143
[58] Field of Search ......................................... 361/143

[56] References Cited

U.S. PATENT DOCUMENTS

| | | | |
|---|---|---|---|
| 3,335,377 | 8/1967 | Kohlhagen | 335/284 |
| 3,893,059 | 7/1975 | Nowak | 338/32 |
| 4,381,492 | 4/1983 | Steingroever et al. | 361/143 X |

FOREIGN PATENT DOCUMENTS 1575680  9/1980  United Kingdom .

Primary Examiner—Michael L. Gellner
Attorney, Agent, or Firm—John Francis Moran

[57] ABSTRACT

Disclosed are a method of detecting a magnetic preorientation in mechanical parts, such as motor rotors, and a device, utilizing this method, for the magnetization of tubular parts. The device includes a magnetization winding to accommodate the tubular part and an associated magnetizing apparatus. According to the invention, the part (100) is first magnetized near the surface by means of a recording head (300) in such a manner that discrete bar magnets (121 to 132) are formed on the surface between the preoriented zones in the circumferential direction, their lines of flux running between their poles in the preferred direction of the preoriented material, There originate in the preoriented pole zones outside stray fields of twice the number of poles used to position the part (100) during magnetization. In an associated device are provided, in addition to the magnetizing winding (200, 400), a recording head (300), at least one Hall generator (300, 340), and means for moving the parts (100) relative to the magnetizing winding (200, 400).

15 Claims, 8 Drawing Figures

METHODS FOR DETECTING A MAGNETIC PREORIENTATION IN MECHANICAL PARTS AND FOR MAGNETIZING THE PARTS UTILIZING SUCH DETECTION METHOD, AND AN ASSOCIATED DEVICE FOR MAGNETIZING THE PARTS IN ACCORDANCE WITH THESE METHODS

BACKGROUND OF THE INVENTION

The invention relates to a method of detecting a magnetic preorientation in mechanical parts such as motor rotors; to the application of this method when magnetizing these parts; and to an associated device for magnetizing the parts according to these methods.

Rotors for stepping motors consist of a support with a shait and the actual tube magnet. The tube magnet—also called the "rotor"—is usually magnetized to have two to twelve poles; i.e., there are, in circumferential direction, alternately up to six north and six south poles which extend the entire axial length of this part.

To make handling easier, such a rotor with a tube magnet should be magnetized only immediately before installation in the stator. They are magnetized in a device consisting, for example, of a single copper rod winding having six turns within a laminated iron core. The so-called rotor or tube is inserted into the middle of the lamination pack for magnetization and the winding is energized by a capacitor discharge.

In order to obtain optimal magnetization, the manufacturer of the magnet material forming the tube usually magnetically preorients the pole areas near the surface. Because of this preorientation, the rotor must be rotated to a correct pole pitch position inside the magnetizing device prior to the actual magnetization.

In practice, the rotor tube magnet consists, in particular, of barium ferrite which can be powder-metallurgically molded into appropriate parts by pressing and sintering. To increase the remanence of the magnet material, a magnetic field is applied already during the powder-metallurgical manufacturing process in such a manner that the specified magnetic preferred directions are formed in the part.

Since the magnetically preoriented rotor zones are not physically visible, special procedures are needed to rotate the rotors into the correct pitch position prior to full magnetization.

Conventionally, this is done by adding an additional impedance in series with the magnetizing winding so that, at first, a slowly rising excitation current causes the free-turning rotor to rotate into the correct position. The main pulse for the actual magnetization is then applied to the winding.

There is a problem with this magnetizing technique in that dirt particles may adversely affect the freedom of rotation of the rotor in the magnetizing device so that, in many cases, magnetization will not be optimal.

SUMMARY OF THE INVENTION

It is therefore an object of the invention to provide a method of detecting a magnetic preorientation. This method is to be applicable to the magnetization of preoriented parts in a correct pitch position, for which purpose an associated device is to be provided.

This object, as well as other objects which will become apparent in the discussion that follows are achieved, according to the invention, in that the part is magnetized near the surface by means of a recording head in such a manner that discrete bar magnets form on the surface in the circumferential direction between the preoriented zones, their lines of flux running between their poles in the preferred direction of the preoriented material.

The method according to the invention makes it possible to scan the position of the magnetic preorientation in simple manner by means of Hall generators because outer stray fields of twice the number of poles originate in the preoriented pole zones. This makes it possible to apply the method according to the invention advantageously for positioning when magnetizing motor rotors. An associated magnetizing device with a magnetizing winding and a magnetizing apparatus can be supplemented for this purpose so that a recording head and at least one Hall generator are mounted above the magnetizing coil and, after detection of the position of the preorientation and appropriate rotation, the rotor can be inserted in the correct position into the magnetizing winding by means of a lifting device and guide blocks.

Besides the detection of a magnetic preorientation specifically in tubular magnets, the method according to the invention can also be applied to other mechanical part shapes where the position of the preorientation cannot be detected directly from the geometry.

For a full understanding of the present invention, reference should now be made to the following detailed description of the preferred embodiment of the invention and to the accompanying drawings.

DESCRIPTION OF THE PREFERRED EMBODIMENT

Figure 1:
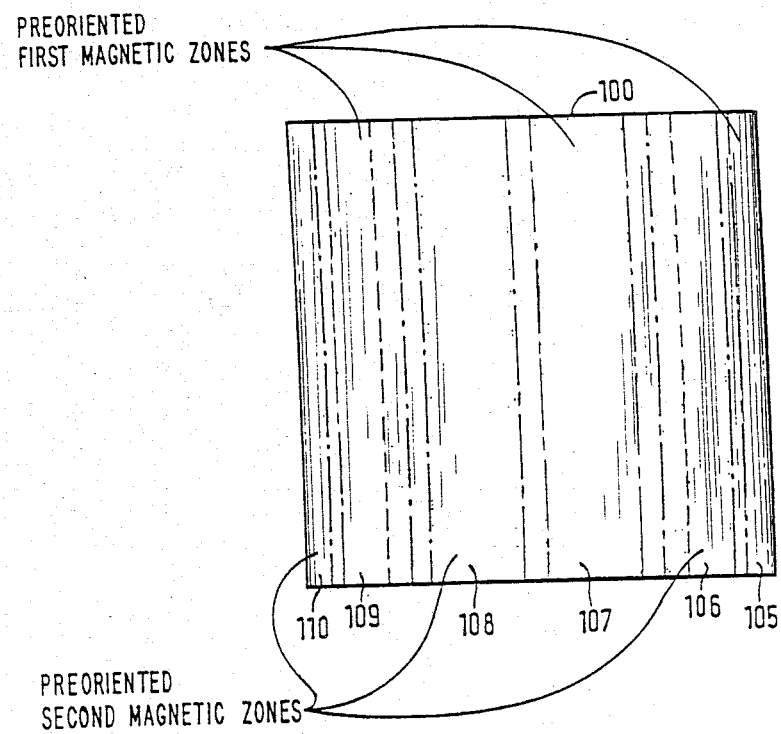
FIG. 1 is a side view of a tubular magnet, for use as a rotor in a stepping motor, with its magnetization indicated.
Figure 2:
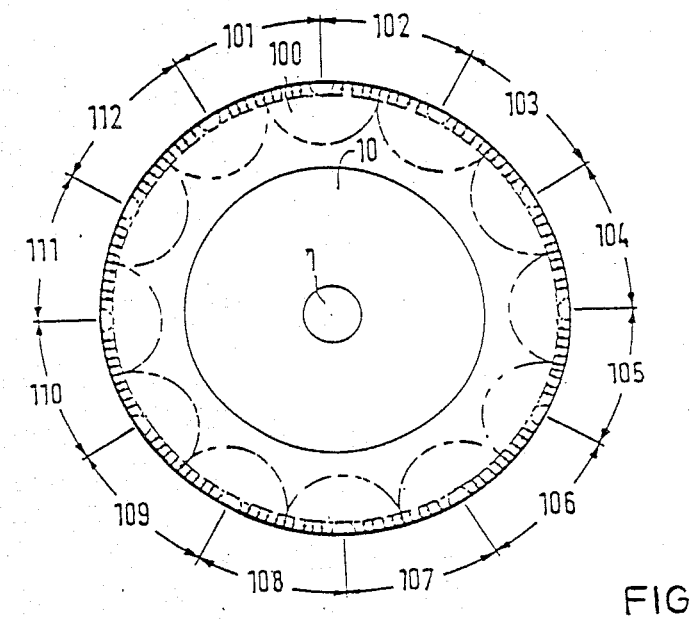
FIG. 2 is a top view of the rotor shown in FIG. 1.

The various figures are not in true scale relative to each other. Identical parts have been given the same reference numbers throughout. The figures are described, partly together, in the following:

FIGS. 1 and 2 depict a tuhe magnet 100 whIch is magnetized on its outside surface. ln the circumferential direction, there are alternately six north and six south poles which, as shown in FIG. 1, extend the entire axial length of the rotor 100 forming the tube magnet. The individual, magnetized zones of respectively opposite lines of flux are designated 101 to 112 according to FIG. 2. A corresponding structure is indicated in the side view of FIG. 1.

Rotors for stepping motors are produced from such parts. For this purpose, the tube magnets 100 are provided in their interior with a support 10 which has a concentric shaft 1 for rotation.

Such motor rotors are usually magnetized in so-called magnetizing windings, an operation called "coining". To obtain a high magnet energy in the coining operation, the rotors consist of preoriented barium ferrite or similar materials, which are provided in the powder-metallurgical fabrication of such molded parts. Prior to the actual magnetization, rotors 100 were previously rotated to the suitable pole pitch position inside the magnetizing coil by means of a prepulse, which requires that the rotor 100 must be accelerated or stopped within a few milliseconds.

Figure 3:
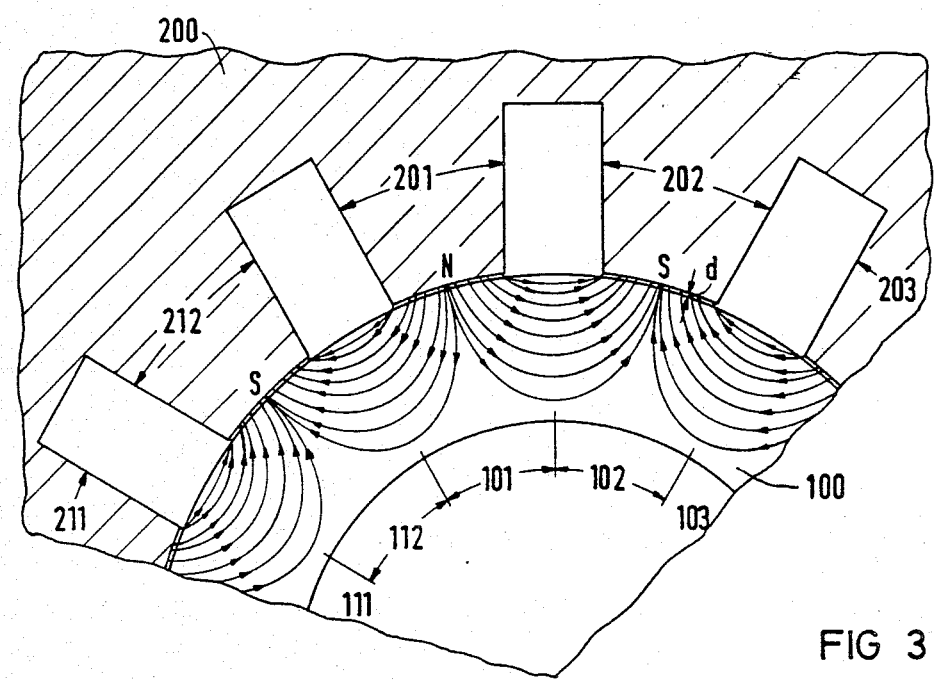
FIGS. 3 and 4 are representational diagrams, each in partial section, illustrating the magnetization of the part according to FIGS. 1 and 2, by means of a magnetizing winding, with the part arranged in two different pole pitch positions.

In FIG. 3 the rotor 100 is shown inside a magnetizing winding after having been rotated to the correct pole pitch position. The reference number 200 designates the turns of a magnetizing winding within a core structure formed of iron laminations (not detailed in FIG. 3). These turns are placed concentrically so that twelve pole shoes 201–212 are formed, the north or south poles resulting alternately through dc excitation due to a meandering winding arrangement in the turns.

There is a gap d approximately 30 μm wide between the winding inside diameter and the rotor outside diameter. If magnetization takes place in this correct pole pitch position, the lines of flux shown in FIG. 3 will result, thereby achieving the magnetization in accordance with the preorientation, as required according to FIG. 2.

Figure 4:
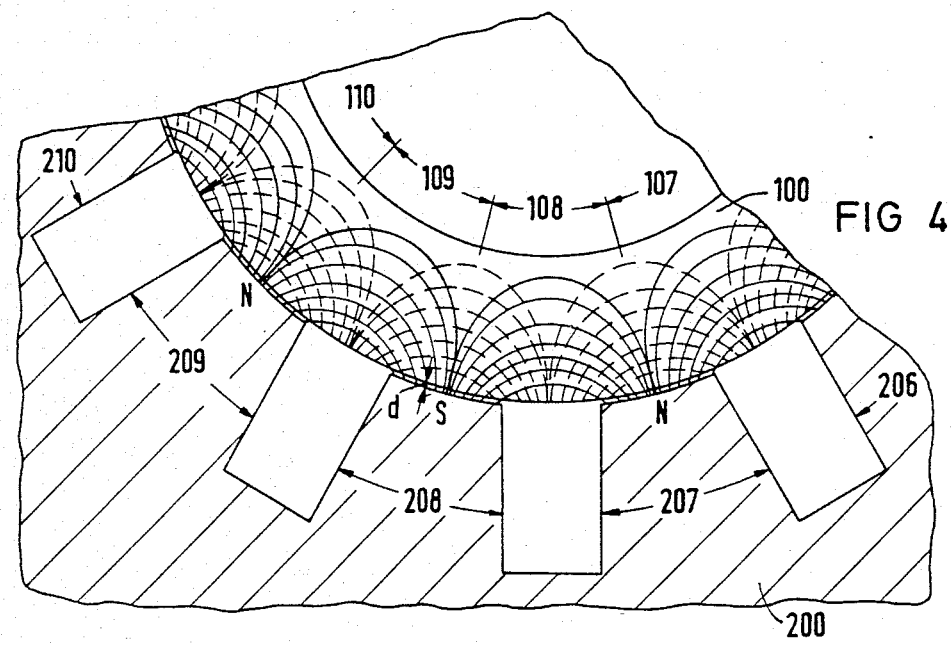

The previously known, conventional magnetizing method works perfectly only if the rotor 100 can move nearly without friction in the magnetizing coil 200 and when the given number of poles is low. In practice, however, turning the rotor to the proper pole pitch position is hindered by dust particles or static friction, which is unavoidable due to the close spacing. In the worst case, the rotor can be magnetized when in the position shown in FIG. 4. In this case, the lines of flux of the preoriented zones 101–112 in the rotor 100 overlap the lines of flux of the pole shoes 201–212, respectively, of the magnetizing winding 200, these lines being largely perpendicular to each other. Therefore, the actual magnetization occurs outside the preoriented pole pitch so that the magnet energy applied is considerably less than that which is theoretically achievable.

An analysis of the physical data of the preoriented rotors shows that zones are present at their respective surfaces which differ widely in their magnetic conductivity. As may be seen from FIG. 3, these material zones under the pole shoes are aligned in a radial direction whereas, under the windings, they are preferably arranged in the circumferential direction. As will be described below, this regularity can be utilized for the detection of the zones themselves.

Figure 5:
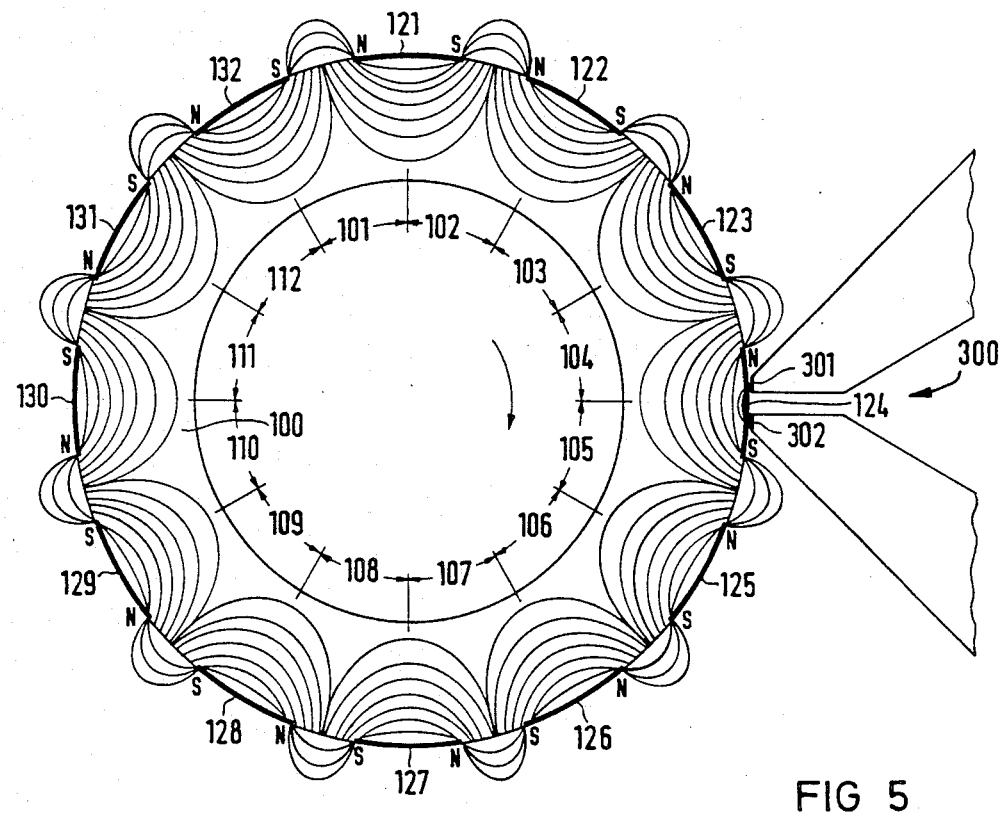
FIG. 5 is a representational diagram illustrating the generation of bar magnets near the surface of a part by means of a recording head.

FIG. 5 shows a rotor 100 with its magnetized zones 101 and 112 being moved past a recording head 300 with two pole shoes 301 and 302. The narrow gap between the pole shoes 301 and 302 of the recording head 300 causes a narrow, steady stray field to be generated. If the rotor is rotated past this stray field, its entire circumference can be magnetized near the surface with a magnetization depth of approximately 0.3 to 0.5 mm, for example. Now, due to the different magnetic surface conductivity of the material, bar magnets 121–132 are formed in the zones of the circumferentially oriented preorientation of the material, whereas especially the radially oriented pole zones remain almost nonmagnetic. The longitudinal magnetization thus produced at the circumference can now be measured in simple manner with magnetic flux-sensitive Hall generators.

Figure 6:
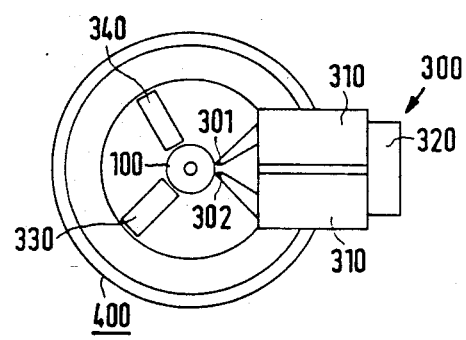
FIG. 6 is a representational diagram showing the recording head with associated Hall generators as measuring elements.

Such an arrangement is shown in FIG. 6 in which the rotor 100 and the recording head 300 with yoke 310, end part 320 and pole shoes 301 and 302 are again present. Two Hall generators 330 and 340 are disposed opposite the recording head 300 with mutual symmetry. A signal curve produced by one of the Hall generators 330 or 340, when the surface-magnetized rotor 100 is rotated, is shown in FIG. 7 and explained below.

To record a circumferentially oriented magnetization on the rotor 100, the recording head 300 is dc-energized and turned on for about 1.5 seconds for one complete revolution of a rotor 100. During one revolution of the rotor 100, not only do differences in the magnetic field strength result on the surface, but also differences in the number of poles. Due to the formation of bar shaped magnets in the pitch zone of the windings, the stray flux of each of these magnets is directed towards its own counterpole in the preferred direction of the preoriented zone. Therefore, little or no stray flux appears outside the rotor in these zones. In constrast thereto, in the pole zones corresponding to the magnetizing winding, the extension of the magnets towards their respective adjacent poles is hindered by the radial material arrangement. Here, the magnetic flux extends outside the rotor, resulting in the creation of twelve north poles and twelve south poles. This is evident from considering both FIGS. 5 and 7 and has been confirmed by measurement.

Figure 7:
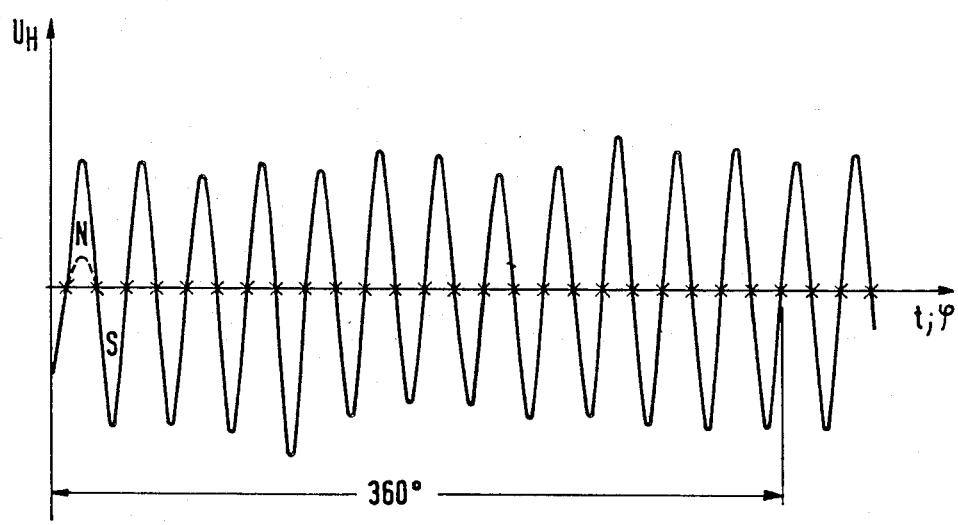
FIG. 7 is a graph showing a test signal recorded by means of Hall generators.

The test curve shown in FIG. 7 is approximately sine shaped, corresponding to the longitudinal magnetization. The pole pitch can be determined in detail by the respective zero crossings and the polarity of the Hall voltage. In addition, the signal of the second Hall generator 340, which is offset relative to the Hall generator 330, may also be used.

In measuring the Hall voltage, the relative height of the signal amplitude is not utilized; only the zero crossings are utilized. Since the latter are specific for the magnetization position, they can be used for correct pole pitch positioning.

Figure 8:
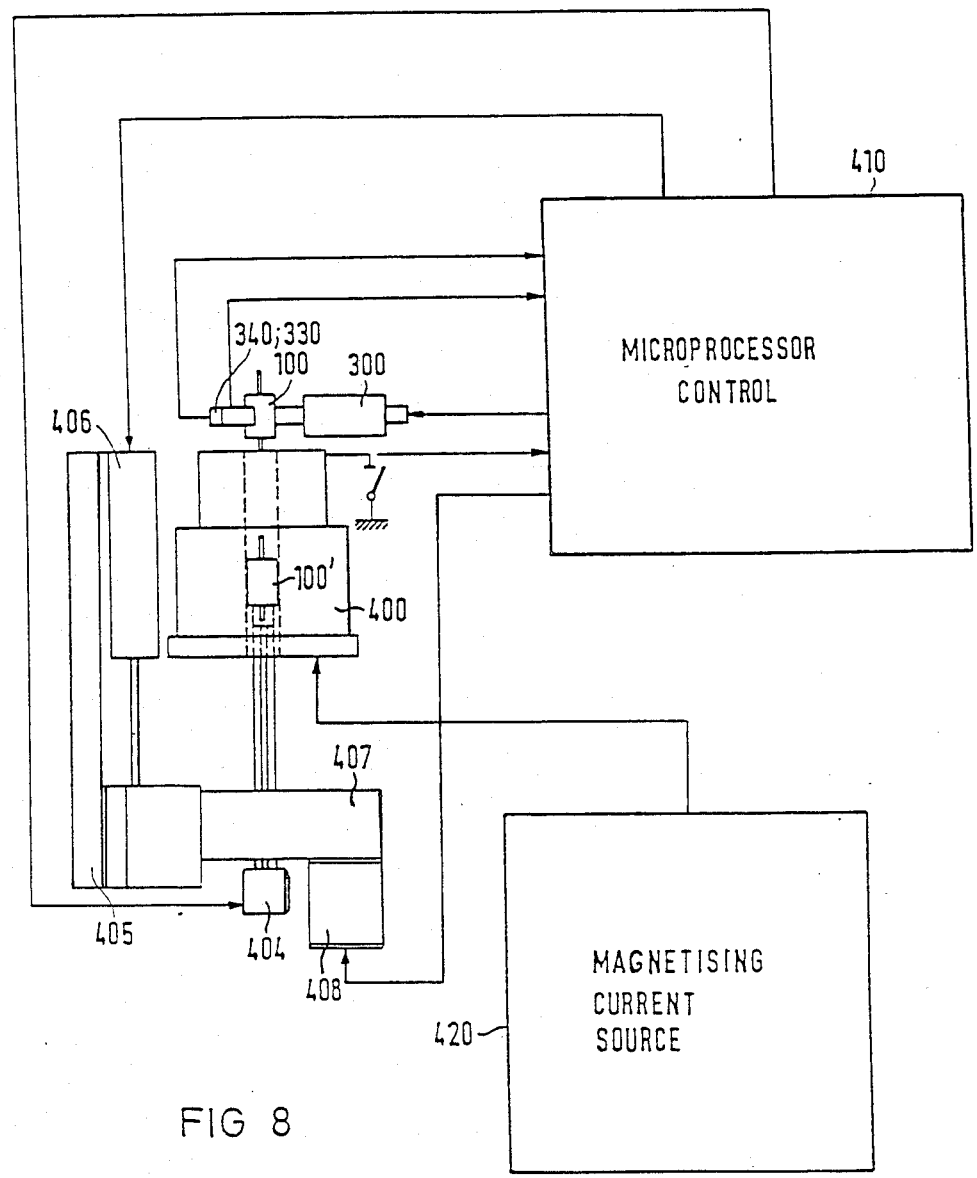
FIG. 8 is a schematic diagram of a magnetizing device according to the invention.

FIG. 8 shows a device ior magnetizing motor rotors using the above described method. A stationary carriage 405 with a lifting cylinder 406, a transmission 407 and an associated drive motor 408 are coordinated therein with a magnetizing winding per FIG. 3 fixed in a housing 400. This arrangement provides for the motion of the rotor 100 relative to the stationary housing 400 of the magnetizing winding, whereby the rotor can be inserted into the housing 400 of the magnetizing winding by a linear motion after having been rotated to its proper pole pitch position. A clamping magnet 404 is provided for holding the rotor 100. Also coordinated with the magnetizing device is a microprocessor 410 for Hall signal processing and cycle control, as well as a conventional apparatus 420 for generating a magnetizing pulse.

The magnetizing procedure is as follows: After placing the rotor 100 into the clamping magnet 404 outside the magnetizing housing 400, the rotor 100 is moved under slight contact pressure past the turned-on recording head 300 and thereby surface-magnetized. During rotation by 370 degrees (one turn + 10 degrees), the Hall voltage signal $U_H$ is picked up by the Hall generators 330 and 340 and transmitted to the microprocessor unit 410. The control cycle is then activated upon processing the signals, thereby turning the rotor 100 into the required, proper pole pitch position by means of the drive motor 408 and transmission 407. The clamping magnet 404, including the rotor 100, is inserted into the magnetizing winding by means of the mechanical lifting device 405/406, whereupon the magnetic coining can take place directly by the magnetizing apparatus. Since the rotor 100 is now non-positively driven by the rotary drive outside the magnetizing winding 400, dust particles or static friction can not have an effect. On the other hand, the lowering motion can be performed precisely so that the magnet energy is now utilized to the optimum by the magnetizing device. In addition, because the Hall generators are disposed outside the magnetizing winding, it is now possible to check the quality of the magnetization directly thereafter by quantitive measurements.

There has thus been shown and described novel methods for detecting a magnetic preorientation in mechanical parts, and for magnetizing the parts utilizing such detection, and associated apparatus for magnetizing the parts in accordance with these methods, which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope oi the invention are deemed to be covered by the invention which is limited only by the claims which follow.

What is claimed is:

1. A method of detecting a magnetic preorientation in a mechanical part, such as a motor rotor, comprising the steps of:
    moving the surface of said part past a recording head, thereby to form discrete bar magnets near the surface of said part between its preoriented zones, the lines of flux of said bar magnets extending between their poles in the preferred direction of the preoriented material of said part; and
    detecting the surface magnetization of said part.

2. The method defined in claim 1, wherein said part has rotational symmetry, said surface being moved past said recording head by rotation of said part, thereby to form said bar magnets in the circumferential direction of said part.

3. The method defined in claim 1, wherein said surface is moved past said recording head with a slight contact pressure against said head.

4. The method defined in claim 1, wherein direct current is applied to said recording head.

5. The method defined in claim 1, wherein said detecting step comprises the step of scanning the surface magnetization of said part by means of at least one Hall generator.

6. The method defined in claim 5, wherein said at least one Hall generator includes two Hall generators.

7. The method defined in claim 5, further comprising the step of positioning of said part in dependence upon the signal produced by said at least one Hall generator.

8. The method defined in claim 2, further comprising the steps of:
    rotating said part to align it with the pole pitch position of a magnetizing winding;
    while fixed in position, inserting said part into said magnetizing winding; and
    energizing said magnetizing winding to magnetize said part in correct alignment with the detected magnetic preorientation of said part.

9. Apparatus for magnetizing tubular mechanical parts, such as motor rotors, comprising, in combination:
    (a) a magnetizing winding constructed to accommodate said parts;
    (b) means for supplying electrical energy to said winding;
    (c) a recording head arranged outside of said winding;
    (d) at least one Hall generator arranged outside of said winding; and
    (e) means for moving said parts, without changing their orientation, from an adjacent relationship with respect to said recording head and said at least one Hall generator to an adjacent relationship with respect to said winding.

10. The apparatus defined in claim 9, wherein said means for moving said parts includes:
    (1) a clamp, mounted in the axial plane of said winding;
    (2) motor drive means for rotating said clamp; and
    (3) lifting cylinder means for inserting said parts in said winding.

11. The apparatus recited in claim 10, wherein said motor drive means and said lifting cylinder are mounted on a guide carriage.

12. The apparatus defined in claim 9, wherein said recording head and said at least one Hall generator are arranged in opposing relationship.

13. The apparatus defined in claim 9, wherein said at least one Hall generator includes two Hall generators which are symmetrically arranged with respect to said recording head.

14. The apparatus defined in claim 9, further comprising control means for regulating the cycles of operation of said apparatus.

15. The apparatus defined in claim 14, wherein said control means is a microprocessor.

* * * * *